United States Patent
Nino et al.

(10) Patent No.: US 9,949,780 B2
(45) Date of Patent: *Apr. 24, 2018

(54) MEDICAL TOOL AND WASTE COLLECTION DEVICE

(71) Applicant: ECA Medical Instruments, Newbury Park, CA (US)

(72) Inventors: John Nino, Simi Valley, CA (US); David Ivinson, Camarillo, CA (US)

(73) Assignee: ECA MEDICAL INSTRUMENTS, Newbury Park, CA (US)

( * ) Notice: Subject to any disclaimer, the term of this patent is extended or adjusted under 35 U.S.C. 154(b) by 261 days.

This patent is subject to a terminal disclaimer.

(21) Appl. No.: 14/862,972

(22) Filed: Sep. 23, 2015

(65) Prior Publication Data

US 2016/0008523 A1 Jan. 14, 2016

Related U.S. Application Data

(63) Continuation of application No. 13/983,535, filed as application No. PCT/US2012/024731 on Feb. 10, 2012, now Pat. No. 9,173,813.

(Continued)

(51) Int. Cl.
*A61J 1/05* (2006.01)
*A61B 17/29* (2006.01)
(Continued)

(52) U.S. Cl.
CPC .......... *A61B 17/8875* (2013.01); *A61B 17/16* (2013.01); *A61B 17/29* (2013.01);
(Continued)

(58) Field of Classification Search
CPC ..... A61B 17/8875; A61B 17/16; A61B 17/29; A61B 17/32; A61B 17/320016;
(Continued)

(56) References Cited

U.S. PATENT DOCUMENTS

| 267,517 A | 11/1882 | Gray |
| D37,997 S | 5/1906 | Tower |

(Continued)

FOREIGN PATENT DOCUMENTS

| EP | 2168539 A2 | 3/2010 |
| KR | 20-0353368 | 6/2004 |

(Continued)

OTHER PUBLICATIONS

Canadian Office Action dated Sep. 11, 2014, Issued in Canadian Patent Application No. 2,826,763.

(Continued)

*Primary Examiner* — David B Thomas
(74) *Attorney, Agent, or Firm* — Baker & Hostetler LLP

(57) ABSTRACT

A welled handle device comprising a base with a front and back end having a predetermined grippable silhouette or outer contour, a plurality of open wells formed in the base, and a tool portion connected to the front end of the base. The open wells contain regions which are substantially rough or textured and regions which are substantially smooth. A method of collecting medical waste comprising the steps of having waste on a hand or glove and gripping the grippable outer contour of the welled handle device, wherein at least some of the medical waste is collected within the wells of the handle.

4 Claims, 6 Drawing Sheets

Related U.S. Application Data

(60) Provisional application No. 61/463,041, filed on Feb. 12, 2011.

(51) Int. Cl.

| | | |
|---|---|---|
| *A61B 17/16* | (2006.01) | |
| *A61B 19/02* | (2006.01) | |
| *A61B 17/88* | (2006.01) | |
| *A61B 17/32* | (2006.01) | |
| *A61B 19/00* | (2006.01) | |
| *A61B 17/00* | (2006.01) | |
| *A61B 90/70* | (2016.01) | |
| *A61B 50/36* | (2016.01) | |
| *A61B 50/37* | (2016.01) | |

(52) U.S. Cl.
CPC ...... *A61B 17/32* (2013.01); *A61B 17/320016* (2013.01); *A61B 50/36* (2016.02); *A61B 50/362* (2016.02); *A61B 50/37* (2016.02); *A61B 90/70* (2016.02); *A61B 2017/0023* (2013.01); *A61B 2017/0042* (2013.01); *A61B 2017/0046* (2013.01); *A61B 2017/00424* (2013.01); *A61B 2017/00429* (2013.01)

(58) Field of Classification Search
CPC ....... A61B 50/36; A61B 50/362; A61B 50/37; A61B 90/70; A61B 2017/0023; A61B 2017/0042; A61B 2017/00424; A61B 2017/00429; A61B 2017/0046
See application file for complete search history.

(56) References Cited

U.S. PATENT DOCUMENTS

| | | | |
|---|---|---|---|
| 3,803,667 A | 4/1974 | Rose | |
| 4,091,497 A | 5/1978 | Bade | |
| 4,414,974 A | 11/1983 | Dotson et al. | |
| D318,118 S | 7/1991 | Michelson | |
| D331,625 S | 12/1992 | Price | |
| D336,957 S | 6/1993 | Koros | |
| 5,391,171 A | 2/1995 | Schmieding | |
| 5,464,407 A | 11/1995 | McGuire | |
| 5,489,307 A | 2/1996 | Kuslich et al. | |
| D379,510 S | 5/1997 | Bays | |
| 6,416,518 B1 | 7/2002 | DeMayo | |
| D490,896 S | 6/2004 | Bogazzi | |
| 6,960,206 B2 | 11/2005 | Keane | |
| D513,378 S | 1/2006 | Lin | |
| D520,320 S | 5/2006 | Corcoran | |
| D531,310 S | 10/2006 | Wolter et al. | |
| D551,052 S | 9/2007 | Lin | |
| D553,464 S | 10/2007 | Rinner | |
| 7,334,509 B1 | 2/2008 | Gao | |
| 7,488,326 B2 | 2/2009 | Elliott et al. | |
| D619,716 S | 7/2010 | Wagner | |
| D627,882 S | 11/2010 | Slowley et al. | |
| D646,545 S | 10/2011 | Molina et al. | |
| D652,137 S | 1/2012 | Nino et al. | |
| D652,138 S | 1/2012 | Nino et al. | |
| 8,236,010 B2 | 8/2012 | Ortiz et al. | |
| 8,287,538 B2 | 10/2012 | Brenzel et al. | |
| 8,361,078 B2 | 1/2013 | Beyar et al. | |
| D700,033 S | 2/2014 | Lin | |
| 8,814,935 B2 | 8/2014 | Paulos | |
| 8,906,022 B2 | 12/2014 | Krinke et al. | |
| D724,201 S | 3/2015 | Homsy | |
| 9,060,748 B2 | 6/2015 | Housman et al. | |
| D737,443 S | 8/2015 | Ciravolo et al. | |
| 9,173,813 B2* | 11/2015 | Nino | A61B 17/29 |
| 9,220,554 B2 | 12/2015 | O'Halloran et al. | |
| 2002/0114920 A1 | 8/2002 | Scholz et al. | |
| 2003/0023247 A1 | 1/2003 | Lind et al. | |
| 2003/0070514 A1 | 4/2003 | Kilgore | |
| 2003/0120272 A1 | 6/2003 | Schneider et al. | |
| 2003/0191474 A1 | 10/2003 | Cragg et al. | |
| 2004/0127888 A1 | 7/2004 | O'Neil et al. | |
| 2005/0119663 A1 | 6/2005 | Keyer et al. | |
| 2006/0074374 A1 | 4/2006 | Gresham | |
| 2007/0016219 A1 | 1/2007 | Levine | |
| 2007/0027230 A1 | 2/2007 | Beyar et al. | |
| 2007/0135779 A1 | 6/2007 | Lalomia et al. | |
| 2009/0145901 A1 | 6/2009 | Finnestad et al. | |
| 2009/0198263 A1 | 8/2009 | LaFauci et al. | |
| 2009/0306657 A1 | 12/2009 | Piippo et al. | |
| 2010/0160824 A1 | 6/2010 | Parihar et al. | |
| 2011/0144671 A1 | 6/2011 | Piippo et al. | |
| 2014/0046336 A1* | 2/2014 | Nino | A61C 1/082 606/96 |
| 2014/0276893 A1 | 9/2014 | Schaller et al. | |
| 2015/0223825 A1* | 8/2015 | Nino | A61B 17/17 606/96 |
| 2015/0374426 A1 | 12/2015 | Galm et al. | |
| 2016/0008523 A1 | 1/2016 | Nino et al. | |

FOREIGN PATENT DOCUMENTS

| | | |
|---|---|---|
| WO | WO 2005/021066 A1 | 3/2005 |
| WO | WO 2005/037065 A2 | 4/2005 |
| WO | WO 2010/034847 A1 | 4/2010 |

OTHER PUBLICATIONS

European Search Report dated Jun. 18, 2014, Issued in European Patent Application No. 12745227.4.

* cited by examiner

MEDICAL TOOL AND WASTE COLLECTION DEVICE

RELATED APPLICATION

This application is a Continuation of U.S. Utility patent application Ser. No. 13/983,535 filed Aug. 21, 2013, which claim priority to International patent application PCT/US2012/024731 filed Feb. 10, 2012, which claims the full Paris Convention benefit of and priority to U.S. Provisional Patent Application Ser. No. 61/463,041 filed Feb. 12, 2011, the contents of which are incorporated by reference herein in their entirety, as if fully set forth herein.

BACKGROUND

1. Field

This disclosure relates to medical waste collection with a handle of a hand held disposable medical instrument.

2. General

Properly discarding biological tissue during a surgical procedure is vital to the safety of the staff and the patient. Tissue is considered pathological waste, and after its disposal from the operating room it must be sterilized before it can be sent to a waste site. There is a significant possibility of transmission of infectious diseases if the tissue is simply thrown away in the garbage to decompose. Additionally, all scalpel blades used in the surgery to remove the tissue must be safely disposed of, and any used needles must be deposited into a sharps container.

All biohazard containers and bags must be sent to the sterilization department within the hospital to be either incinerated or autoclaved. States vary on regulations concerning the final disposal of pathological waste.

On a United States Federal level, the storage and management of medical waste is primarily regulated by OSHA. The OSHA regulations only apply to human blood, human infectious wastes, and human pathological wastes. Under OSHA: contaminated reusable sharps must be placed in containers that are: puncture resistant; labeled or color coded; and leakproof on the sides and bottom, reusable sharps that are contaminated with blood or other potentially infectious materials must not be stored or processed in a manner that requires employees to reach by hand into the containers, and specimens of blood or other potentially infectious material are required to be placed in a container that is labeled and color coded and closed prior to being stored, transported or shipped. Contaminated sharps must be placed in containers that are: closeable, puncture resistant, leakproof on sides and bottoms, and labeled or color coded. Regulated wastes (liquid or semi-liquid blood or other potentially infectious materials and contaminated items that would release blood or other potentially infectious materials in a liquid or semi-liquid state if compressed, items that are caked with dried blood or other potentially infectious materials and are capable of releasing these materials during handling, contaminated sharps, and pathological and microbiological wastes containing blood or other potentially infectious materials) must be placed in containers that are: closeable, constructed to contain all contents and prevent leakage of fluids, labeled or color coded, and closed prior to removal. All bins, pails, cans, and similar receptacles intended for reuse, that have the likelihood of becoming contaminated with blood or other potentially infectious materials are required to be inspected and decontaminated on a regularly scheduled basis. Labels affixed to containers of regulated wastes, refrigerators and freezers containing blood or other potentially infectious materials, and other containers used to store, transport, or ship blood or other potentially infectious materials must: include the biohazard symbol, be fluorescent orange or orange-red or predominantly so, with lettering and symbols in contrasting color; and affixed as closely as possible to the container by adhesive or wire to prevent loss or removal. Citation at http://www.fedcenter.gov/assistance/facilitytour/solid/medical/.

One definition of Medical Waste is: Medical waste is all waste materials generated at health care facilities, such as hospitals, clinics, physician's offices, dental practices, blood banks, and veterinary hospitals/clinics, as well as medical research facilities and laboratories.

The Medical Waste tracking Act of 1988 defines medical waste as "any solid waste that is generated in the diagnosis, treatment, or immunization of human beings or animals, in research pertaining thereto, or in the production or testing of biologicals." This definition includes, but is not limited to:

blood-soaked bandages culture dishes and other glassware discarded surgical gloves discarded surgical instruments discarded needles used to give shots or draw blood (e.g., medical sharps)

cultures, stocks, swabs used to inoculate cultures removed body organs (e.g., tonsils, appendices, limbs)

discarded lancets

Citation at http://www.epa.gov.

DESCRIPTION

According to some exemplary implementations, disclosed is a method to collect medical waste, the method comprising collecting medical waste on a glove or hand of a user by griping a welled handle of a medical tool; and, having at least some of said medical waste be transferred from the glove or hand to being collected within the wells of the handle. In some instances, the welled handle with medical waste collected in the wells is disposed of. One aspect in some implementations includes a rough surface on at least one wall, defined as being textured or rough enough to facilitate medical waste adherence to the texture.

According to some exemplary implementations, disclosed is a grippable reduced slip handle. Said handle with collection wells collects medical waste off the hand or glove of a user, thereby removing a portion of the fluid, tissue or other material which may cause slippage or reduce grip on said handle.

According to some exemplary implementations, disclosed is a skeleton contour silhouette of a preselected shape with cut-out at the surface forming collection wells. Said contour with cut-outs providing collection recesses for medical waste and removing or directing said waste off the outer contour of the handle and into said wells. In some aspects, the outer silhouette shape has at least a portion which is one of bulb, oval, cylinder, polygon, elongated, conical, pencil curved sided, and planar.

According to some exemplary implementations, disclosed is a medical instrument handle with a self-cleaning grip area. Said grip area has open collection wells wherein some medical waste off may flow from the hand or glove of a user, thereby removing a portion of the medical waste (fluid, tissue or other materials) which otherwise may cause the user's hand to slip or cause the user to have a reduced grip on said handle.

Disposal of the medical waste and handle together is also disclosed.

DRAWINGS

The above-mentioned features and objects of the present disclosure will become more apparent with reference to the following description taken in conjunction with the accompanying drawings wherein like reference numerals denote like elements and in which.

Figure 1:
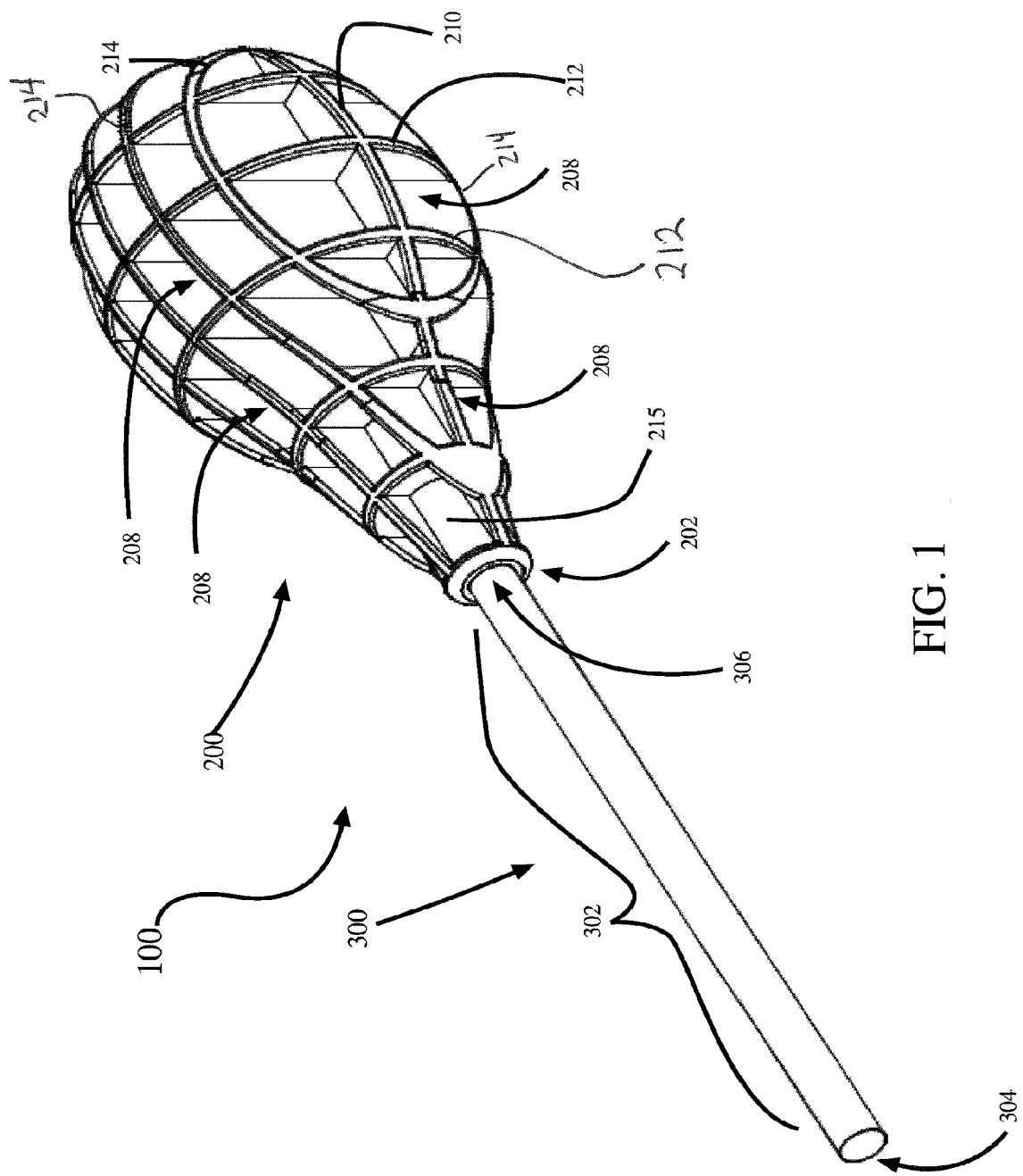
FIGS. 1 and 2 show some aspects of a medical tool with waste collection.

All descriptions and callouts in the Figures are hereby incorporated by this reference as if fully set forth herein.

FURTHER DESCRIPTION

According to some exemplary implementations, a medical instrument/tool/device 100 comprises a handle 200 portion and a tool portion 300 with a body 302 that may support a distal tip 304 at its distal end. The handle is a base and may be referred to as a "base". The base should be of a size and shape to allow it to be hand held. Said body 302 may also be a cutting or filing zone. The distal tip may be a mount for a tool such as a socket or it may a type of driver, screwdriver, wrench, cutter, probe, retractor, resector or prod. Tool portion 300 is affixed to handle 200 at a tool-handle interface 202. Tool portion 300 is affixed to handle 200 at its proximal end 306 at a tool-handle interface 202. The affixation is at ether the front end or the back end of said handle (not shown in detail, however the front end shall be the end nearest the tool-handle interface) and the back end shall be the end furthest form that interface.

Figure 2:
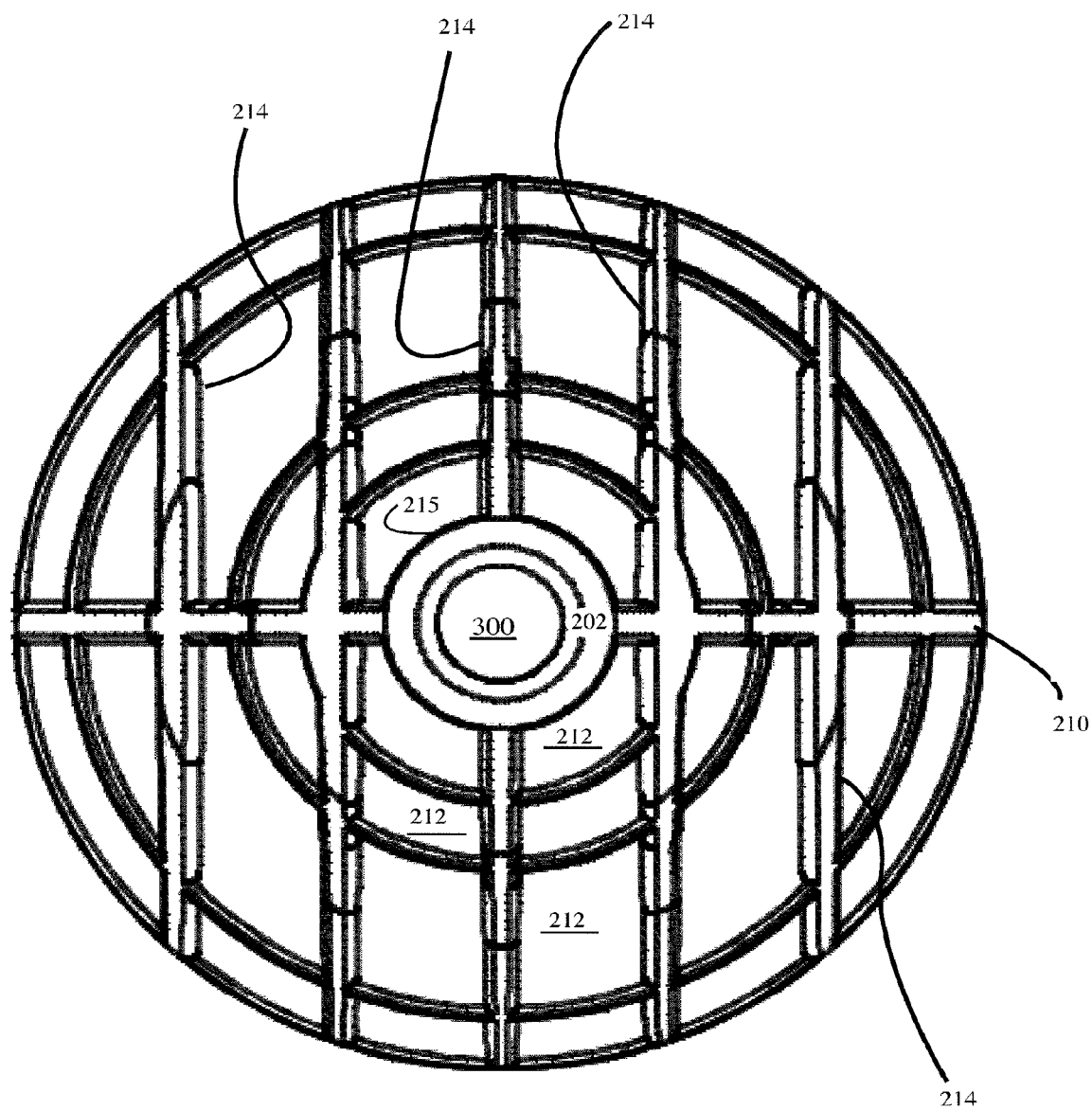

Handle 200 is not solid. Handle 200 has a plurality of deep open wells 208. The handle may also be referred to as a "welled" structure. The deep wells may be 3, 4, or 5 sided. The top (unattached) edge of a series of walls 210, 212, 214 form a grippable outer contour, which for FIGS. 1 and 2 approximates a bulb shape. The open wells 208 are bounded by horizontal walls 210, and intersecting perpendicular walls 212 and 214. In some implementations, a perpendicular wall 212 or 214 or a horizontal wall 210 may also function as a bottom boundary. In some implementations two perpendicular walls 212, and two other perpendicular walls 214 form walls arising from a bottom wall (not shown); such a well is 5-sided. Said horizontal walls rise from a central core 215 and extend radially.

The wells 208 are positioned to collect medical waste from the gloves of a user during procedures. Specifically, human bone, tissue, blood and other fluids are frequently present during procedures. These materials may be medical waste. Medical waste includes:

"Any discarded biologic product such as blood or tissue removed from operating rooms, morgues, laboratories, or other medical facilities. The term may also be applied to bedding, bandages, syringes, and similar materials that have been used in treating patients and to animal carcasses or body parts used in research. Medical waste is regulated at the state and local levels. *Mosby's Medical Dictionary*, 8th edition. © 2009, Elsevier.

Medical waste is regulated and needs to be properly disposed of (see Appendices A, B, and C). Part of the disposal process is the collection of such medical waste. The plurality of wells 208 interface with a user's hand. When properly gloved, the gloved hand of a user will pick-up or be covered with medical waste it is exposed to during medical procedures. The welled structures of the handle are transfer or collection points to acquire, capture or collect medical waste from the hand or gloves of the user during use of said tool. Further, unlike reusable medical device handles which must be sterilize after use and therefore teach away from creating nooks, crannies, cavities and/or wells wherein medical waste may collect, the collection handle herein is disposable and need not be sterilized for reuse.

The material and surface of the wells may be adjusted to correspond to the intended usage. A highly lubricous material may be less adequate in collecting fluid, gooey medical waste. A textured or rough surface may facilitate the collection and retention of medical waste. A combination well wall with a highly smooth and/or slick (or lubricous) upper wall (nearest the open top of a well) and a more textured or rougher region nearer the core that may retain more medical waste. Walls in some instances maybe substantially smooth. Hybrid walls or multi-zone walls may be characterized by a transition between surface features. Said multi-zones may be a bright line transition or a more fuzzy transition. Those of ordinary skill in the art will also recognize that a multi-zone may have a plurality of wall zones of different thickness, texture, properties, geometries, etc.

Figure 3:
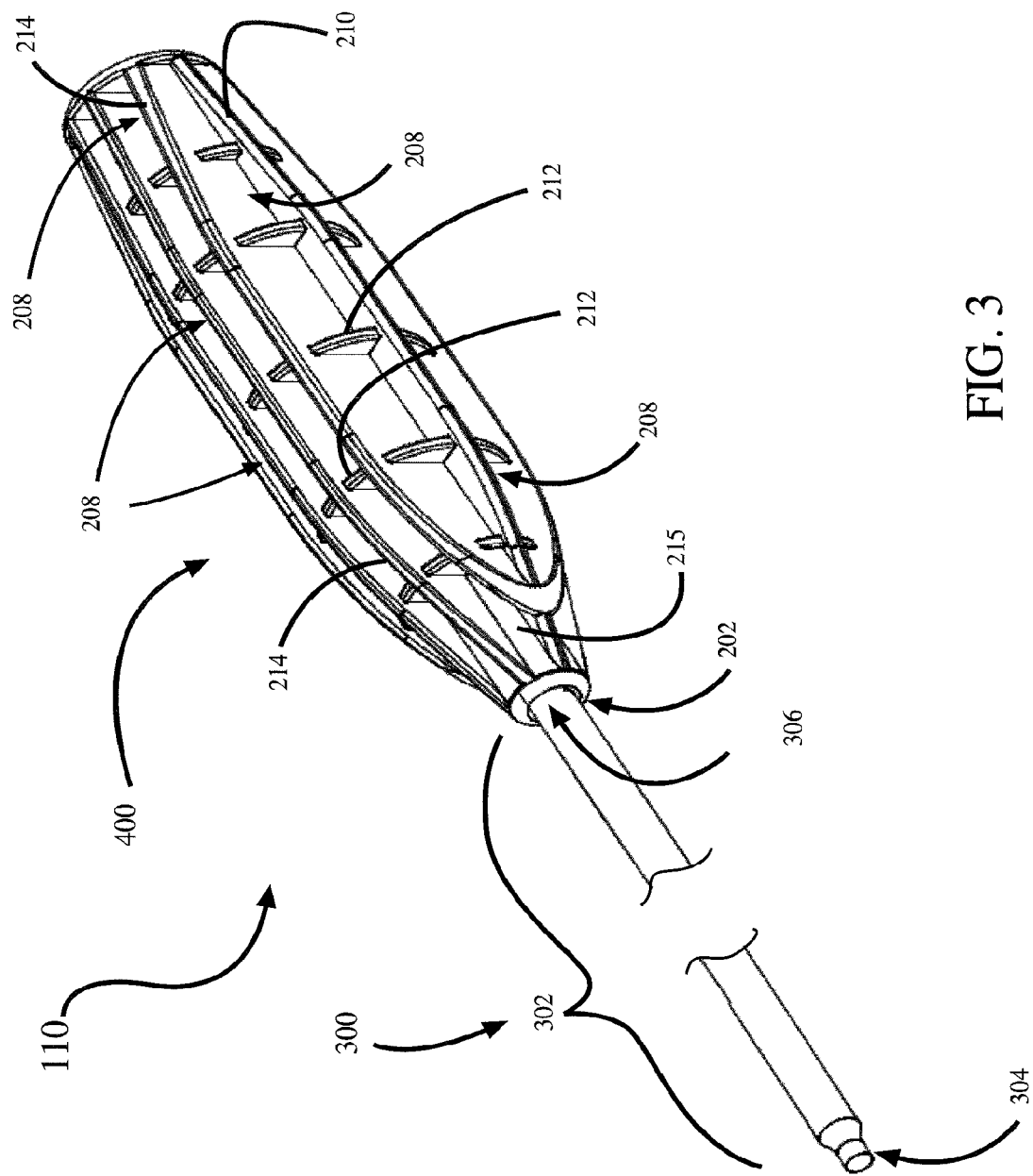
FIGS. 3 and 4 show some aspects of a medical tool with waste collection; and, FIGS. 5 and 6 show some aspects of a medical tool with waste collection.
Figure 4:
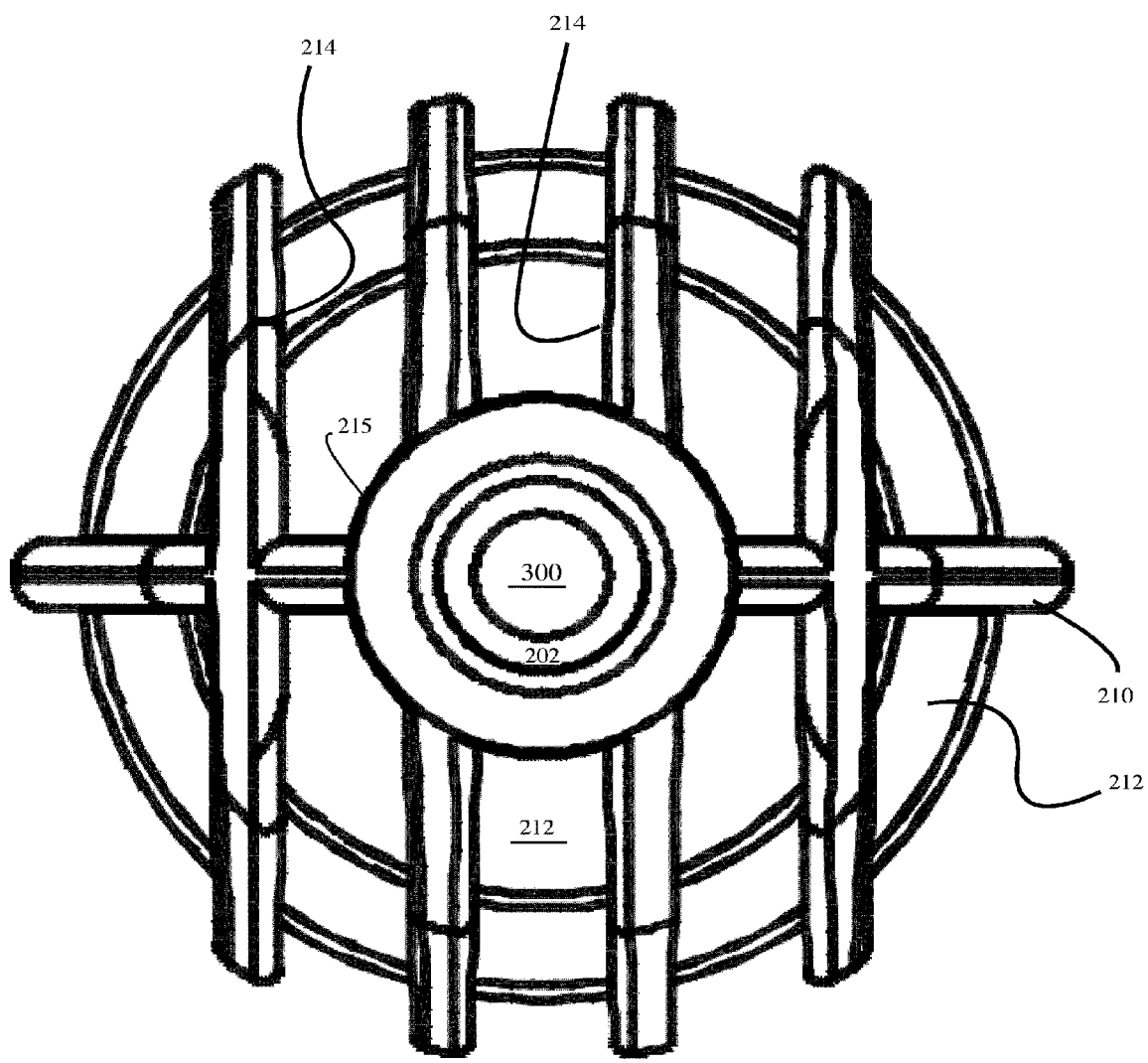

According to some exemplary implementations, a medical instrument/tool/device 110 shown on FIGS. 3 and 4 comprises a handle 400 portion and a tool portion 300 with a body 302 that may support a distal tip 304 at its distal end. The handle should be of a size and shape to allow it to be hand held. Said body 302 may also be a cutting or filing zone. The distal tip may be a mount for a tool such as a socket or it may a type of driver, screwdriver, wrench, cutter, probe, retractor, resector or prod. Tool portion 300 is affixed to handle 400 at a tool-handle interface 202. Tool portion 300 is affixed to handle 400 at its proximal end 306 at a tool-handle interface 202. The affixation is at ether the front end or the back end of said handle (not shown in detail, however the front end shall be the end nearest the tool-handle interface) and the back end shall be the end furthest form that interface.

Handle 400 is not solid. Handle 400 has a plurality of deep open wells 208. The deep wells may be 3, 4, or 5 sided. The top (unattached) edge of a series of walls 210, 212, 214 form a grippable outer contour which for FIGS. 3 and 4 approximates a generally elongated cylinder shape. In some instances, the open wells 208 are bounded by horizontal walls 210, and intersecting perpendicular walls 212 and 214. In some instances, the open wells are bounded by perpendicular walls 212 and 214 and have a bottom boundary wall which may be the central core 215. Said horizontal walls extend from a central core 215 and extend radially. Those of ordinary skill in the art will recognize that the substantially planar walls defining the wells are not a limitation and that non-planar wall structures which surround a collection well are within the scope of this disclosure.

According to some exemplary implementations, a medical instrument/tool/device 120 comprises a handle 500 portion and a tool portion 300 with a body 302 that may support a distal tip 304 at its distal end. The handle should be of a size and shape to allow it to be hand held. Said body 302 may also be a cutting or filing zone. The distal tip may be a mount for a tool such as a socket or it may a type of driver, screwdriver, wrench, cutter, probe, retractor, resector or prod. Tool portion 300 is affixed to handle 500 at a tool-handle interface 202. Tool portion 300 is affixed to handle 500 at its proximal end 306 at a tool-handle interface 202. The affixation is at ether the front end or the back end of said handle (not shown in detail, however the front end shall be the end nearest the tool-handle interface) and the back end shall be the end furthest form that interface.

Figure 5:
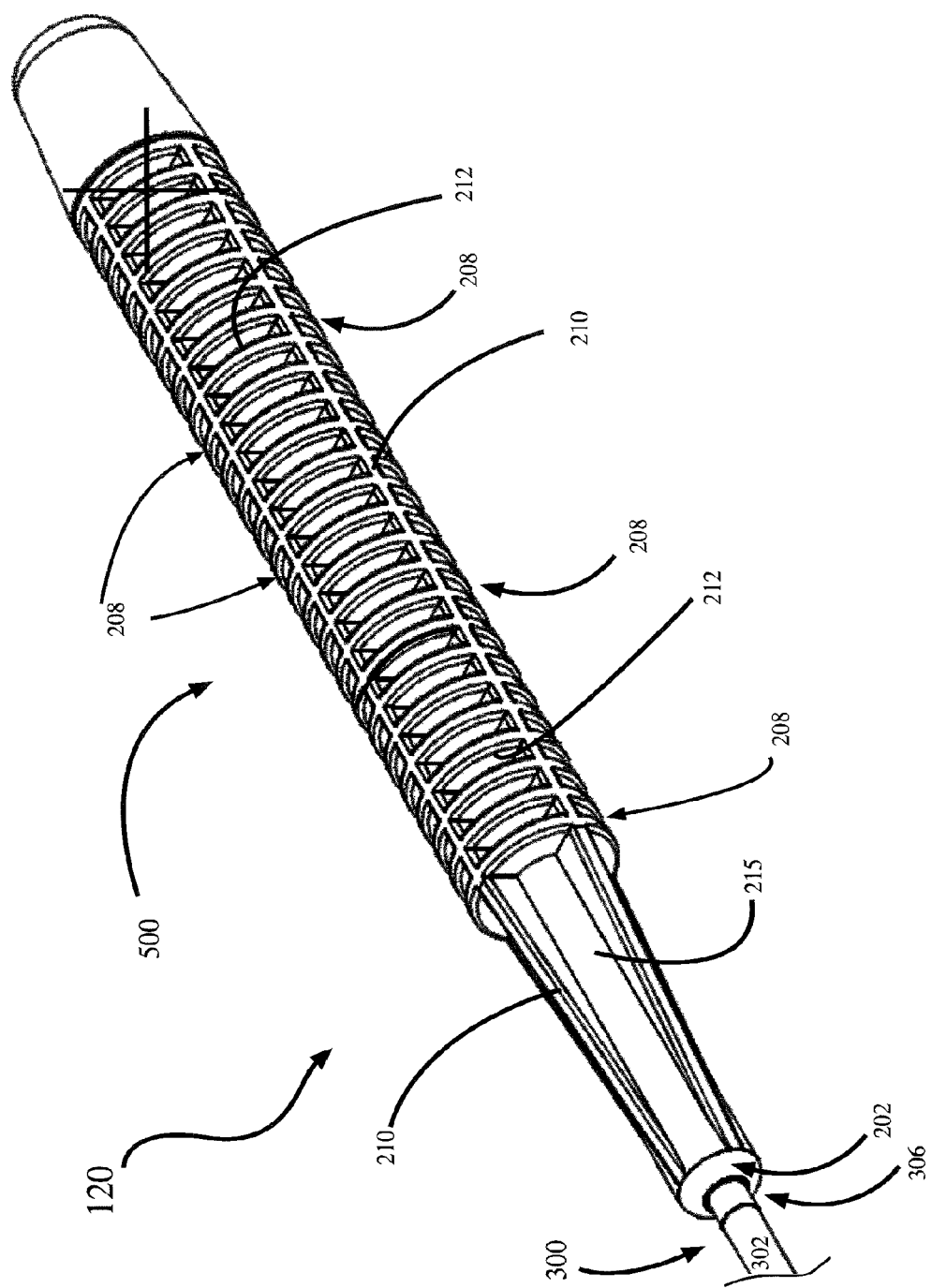
Figure 6:
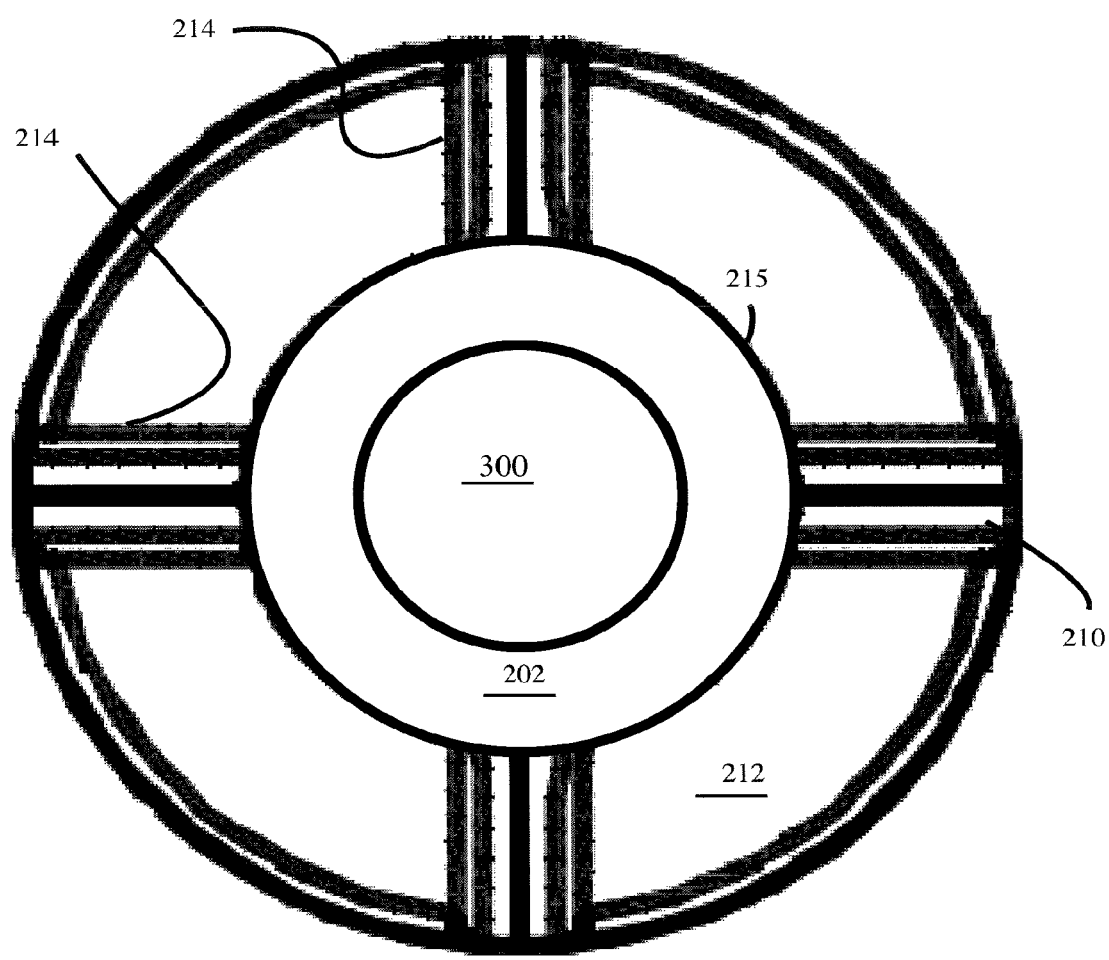

Handle 500 is not solid. Handle 500 has a plurality of open wells 208. The wells are shown 5 sided (left, right, front, back, bottom). The top (unattached) edge of a series of walls 210 and 212 form a grippable outer contour which for FIGS. 5 and 6 approximates a generally pencil cylinder shape. The open wells 208 are bounded by horizontal walls 210, and intersecting perpendicular walls 212. Said horizontal walls rise from a central core 215 and extend radially . Those of ordinary skill in the art will recognize that the substantially planar walls defining the wells are not a limitation and that non-planar wall structures which surround a collection well are within the scope of this disclosure.

Open wells collect medical waste. Via the method of providing a handle having such open wells the user of such a handle will benefit from having medical waste products on the user's hands or gloves flow into collection wells thereby removing the slippery materials from coating all of the handle. In particular having edges of walls forming a silhouette interspersed with wells provides a balance between grippable surface and controlling the coating of medical waste about the area of the handle the user grips. In some instances the outer silhouette shape has at least a portion which are one of bulb, oval, cylinder, polygon, elongated, conical, pencil curved sided, and planar. The outermost edge (from the center core 215 of each instrument handle) of the walls form the silhouette of each handle 200, 200 and 500.

The medial device instrument handles shown in FIGS. 1-6 have self-cleaning. Self-cleaning of of the outer edge of the walls forming the handle silhouette wherein medical waste off may flow from the hand or glove of a user thereby removing a portion of the medical waste (fluid, tissue or other materials) which otherwise may cause the user's hand to slip, or cause the user to have a reduced grip on said handle.

While the method and apparatus have been described in terms of what are presently considered to be the most practical and preferred embodiments, it is to be understood that the disclosure need not be limited to the disclosed embodiments. It is intended to cover various modifications and similar arrangements included within the spirit and scope of the claims, the scope of which should be accorded the broadest interpretation so as to encompass all such modifications and similar structures. The present disclosure includes any and all embodiments of the following claims.

It should also be understood that a variety of changes may be made without departing from the essence of the invention. Such changes are also implicitly included in the description. They still fall within the scope of this invention. It should be understood that this disclosure is intended to yield a patent covering numerous aspects of the invention both independently and as an overall system and in both method and apparatus modes.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these.

Particularly, it should be understood that as the disclosure relates to elements of the invention, the words for each element may be expressed by equivalent apparatus terms or method terms—even if only the function or result is the same.

Such equivalent, broader, or even more generic terms should be considered to be encompassed in the description of each element or action. Such terms can be substituted where desired to make explicit the implicitly broad coverage to which this invention is entitled.

It should be understood that all actions may be expressed as a means for taking that action or as an element which causes that action.

Similarly, each physical element disclosed should be understood to encompass a disclosure of the action which that physical element facilitates.

Any patents, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in at least one of a standard technical dictionary recognized by artisans and the Random House Webster's Unabridged Dictionary, latest edition are hereby incorporated by reference.

Finally, all referenced listed in the Information Disclosure Statement or other information statement filed with the application are hereby appended and hereby incorporated by reference; however, as to each of the above, to the extent that such information or statements incorporated by reference might be considered inconsistent with the patenting of this/these invention(s), such statements are expressly not to be considered as made by the applicant(s).

In this regard it should be understood that for practical reasons and so as to avoid adding potentially hundreds of claims, the applicant has presented claims with initial dependencies only.

Support should be understood to exist to the degree required under new matter laws—including but not limited to United States Patent Law 35 USC 132 or other such laws—to permit the addition of any of the various dependencies or other elements presented under one independent claim or concept as dependencies or elements under any other independent claim or concept.

To the extent that insubstantial substitutes are made, to the extent that the applicant did not in fact draft any claim so as to literally encompass any particular embodiment, and to the extent otherwise applicable, the applicant should not be understood to have in any way intended to or actually relinquished such coverage as the applicant simply may not have been able to anticipate all eventualities; one skilled in the art, should not be reasonably expected to have drafted a claim that would have literally encompassed such alternative embodiments.

Further, the use of the transitional phrase "comprising" is used to maintain the "open-end" claims herein, according to traditional claim interpretation. Thus, unless the context requires otherwise, it should be understood that the term "compromise" or variations such as "comprises" or "comprising", are intended to imply the inclusion of a stated element or step or group of elements or steps but not the exclusion of any other element or step or group of elements or steps.

Such terms should be interpreted in their most expansive forms so as to afford the applicant the broadest coverage legally permissible.

The invention claimed is:

1. A medical waste collection device comprising:
   a handle comprising a generally elongated shape having a front end and back end, the handle further comprising a central core, a plurality of open wells, and a tool-handle interface; and,
   a tool portion comprising a body with a proximal end and a distal end with a distal tip, wherein the tool portion is affixed to the handle at its proximal end at the tool-handle interface;
   wherein the wells are formed by the intersection of horizontal walls and perpendicular walls, regions of which are substantially smooth;
   wherein the horizontal walls rise from the central core and extend radially; and,
   wherein the top edges of the horizontal and perpendicular walls form a grippable outer contour.

2. The device of claim 1 wherein the handle with medical waste collected in the wells is disposable.

3. The device of claim 1, wherein the horizontal and perpendicular walls of the medical waste collection device comprise:
   a region nearest the top edges of the horizontal and perpendicular walls which is substantially smooth;
   a region near the central core which is substantially rough or textured; and
   one or more transitions between regions with different surface features.

4. The device of claim 1, wherein at least a portion of the grippable outer contour is one of bulbous, oval, cylindrical, polygonal, elongated, conical, pencil curved sided and planar.

* * * * *